(12) United States Patent
Tanaka et al.

(10) Patent No.: US 10,295,532 B2
(45) Date of Patent: May 21, 2019

(54) SENSOR

(71) Applicants: KYOCERA CORPORATION, Kyoto (JP); OSAKA UNIVERSITY, Osaka (JP)

(72) Inventors: Hiroyasu Tanaka, Kyoto (JP); Hideharu Kurioka, Kyoto (JP); Eiichi Tamiya, Osaka (JP); Masato Saito, Osaka (JP)

(73) Assignees: KYOCERA CORPORATION, Kyoto (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 15/050,220

(22) Filed: Feb. 22, 2016

(65) Prior Publication Data

US 2016/0169874 A1 Jun. 16, 2016

Related U.S. Application Data

(63) Continuation of application No. PCT/JP2014/071969, filed on Aug. 22, 2014.

(30) Foreign Application Priority Data

Aug. 23, 2013 (JP) .................................. 2013-173630

(51) Int. Cl.
  *G01N 33/53* (2006.01)
  *G01N 29/02* (2006.01)
(52) U.S. Cl.
  CPC ....... *G01N 33/5304* (2013.01); *G01N 29/022* (2013.01); *G01N 33/5308* (2013.01)

(58) Field of Classification Search
  CPC .................. G01N 33/5304; G01N 29/022
  USPC .......................................... 422/404
  See application file for complete search history.

(56) References Cited

U.S. PATENT DOCUMENTS

| | | | |
|---|---|---|---|
| 2004/0028558 A1* | 2/2004 | Pollock | A61B 5/150213 422/408 |
| 2004/0038195 A1* | 2/2004 | Nerenberg | B06B 1/0292 435/4 |
| 2005/0239194 A1 | 10/2005 | Takahashi et al. | |
| 2006/0049047 A1* | 3/2006 | Sato | G01N 27/3272 204/403.01 |
| 2007/0089525 A1* | 4/2007 | Momose | G01L 9/0025 73/753 |

(Continued)

FOREIGN PATENT DOCUMENTS

| | | |
|---|---|---|
| JP | 2004-132962 A | 4/2004 |
| JP | 2005-249491 A | 9/2005 |

(Continued)

*Primary Examiner* — Kathryn Wright
(74) *Attorney, Agent, or Firm* — Duane Morris LLP

(57) ABSTRACT

A sensor is provided with a sensor element which outputs a signal in accordance with a detected object contained in a specimen positioned on a detection part in an element surface and with a package which accommodates the sensor element inside it and has a passage including a space positioned on the element surface. A lower surface of the passage has the element surface and a lower surface of an inflow passage extending toward the space, and a gap is positioned between the lower surface of the inflow passage and the element surface. The element surface is positioned above the lower surface of the inflow passage.

8 Claims, 7 Drawing Sheets

(56) References Cited

U.S. PATENT DOCUMENTS

| | | | |
|---|---|---|---|
| 2007/0131549 A1 | 6/2007 | Cai et al. | |
| 2008/0247264 A1* | 10/2008 | Gabl | B01F 11/0266 |
| | | | 366/127 |
| 2011/0192218 A1* | 8/2011 | Miyamura | B01F 5/0647 |
| | | | 73/64.56 |
| 2014/0224002 A1 | 8/2014 | Fukuura et al. | |
| 2015/0017753 A1 | 1/2015 | Katta | |

FOREIGN PATENT DOCUMENTS

| | | |
|---|---|---|
| JP | 2007-163499 A | 6/2007 |
| JP | 2011-163882 A | 8/2011 |
| JP | 2013-068546 A | 4/2013 |
| WO | WO 2013/015443 A1 | 1/2013 |
| WO | WO 2013/115175 A1 | 8/2013 |

* cited by examiner

SENSOR

CROSS-REFERENCE TO RELATED APPLICATIONS

The present application is a continuation application to International Application No. PCT/JP2014/071969, filed Aug. 22, 2014 which claims priority to JP2013-173630, filed Aug. 23, 2013. The disclosures of these applications are incorporated herein by reference in their entirety.

TECHNICAL FIELD

The present invention relates to a sensor capable of measuring the property of a liquid or components contained in the liquid. Note that, the "liquid" may be any substance having fluidity and may also have a high viscosity.

BACKGROUND ART

As a sensor which outputs a signal in accordance with a detected object contained in a specimen (analyte liquid) positioned on a detection part, there is known a sensor which guides the analyte liquid onto the detection part by a capillary phenomenon (for example Patent Literature 1). Note that, in Patent Literature 1, the detection part is configured by coating a base plate with a reagent, the base plate configuring the lower surface (bottom surface) of a passage for guiding the analyte liquid. Therefore, the lower surface of the passage and the detection part are continuous.

In the sensor described above, sometimes a gap is formed between the lower surface of the passage and the detection part. For example, in a case where a sensor element having a detection part is accommodated in a package, and a passage is formed in that package, a very small gap is formed between the sensor element and the package and in turn a gap is also formed between the lower surface of the passage and an element surface (including the detection part) of the sensor element which should be continuous.

In such a case, the flow of the analyte liquid due to the capillary phenomenon ends up stopping in the gap, therefore the analyte liquid is liable to not reach the top of the element surface (detection part).

Accordingly, it is desired to provide a sensor capable of suitably causing flow due to a capillary phenomenon.

CITATION LIST

Patent Literature

Patent Literature 1. Japanese Patent Publication No. 2005-249491A

SUMMARY OF INVENTION

A sensor according to one aspect of the present invention has a sensor element which has an element surface and outputs a signal in accordance with a detected object contained in a specimen positioned at a detection part in the element surface; and a package which accommodates the sensor element in an internal portion and has a passage including a space positioned on the element surface. A lower surface of the passage has the element surface and a lower surface of an inflow passage extending toward the space. A first gap is positioned between the lower surface of the inflow passage and the element surface. At least a portion of the element surface is positioned above the lower surface of the inflow passage.

A sensor according to another aspect of the present invention has a sensor element which has an element surface and outputs a signal in accordance with a detected object contained in a specimen positioned at a detection part in the element surface; and a package which accommodates the sensor element in an internal portion and has a passage including a space positioned on the element surface. A lower surface of the passage has the element surface and a lower surface of an outflow passage extending from the space to an advancing direction of the specimen. A third gap is positioned between the element surface and the lower surface of the outflow passage. At least a portion of the lower surface of the outflow passage is positioned above the element surface.

A sensor according to still another aspect of the present invention has a sensor element which has an element surface and outputs a signal in accordance with a detected object contained in a specimen positioned in a detection part in the element surface; and a package which accommodates the sensor element in an internal portion and has a passage including a space positioned on the element surface. A concave portion is provided in a lower surface of the passage. In the passage, at least a portion of a lower surface on a downstream side with respect to the concave portion is positioned above a lower surface on an upstream side.

According to the above configurations, the analyte liquid reaching the gap (concave portion) can easily contact the lower surface on the downstream side. As a result, it becomes easy for the flow due to the capillary phenomenon to pass over the gap.

DESCRIPTION OF EMBODIMENTS

Below, embodiments of the sensor according to the present invention will be explained in detail with reference to the drawings. Note that, in the diagrams explained below, configurations which are the same or similar are assigned the same notations. Further, in the diagrams, each portion is diagrammatically shown and sizes etc. of the portions are sometimes different from the actual ones.

Further, in the sensor, any direction may be defined as upward or downward. In the following description, for convenience, an orthogonal coordinate system "xyz" will be defined, the positive side of the z-direction will be defined as upward, and "upper surface", "lower surface", or other terms will be used.

First Embodiment

Figure 1:
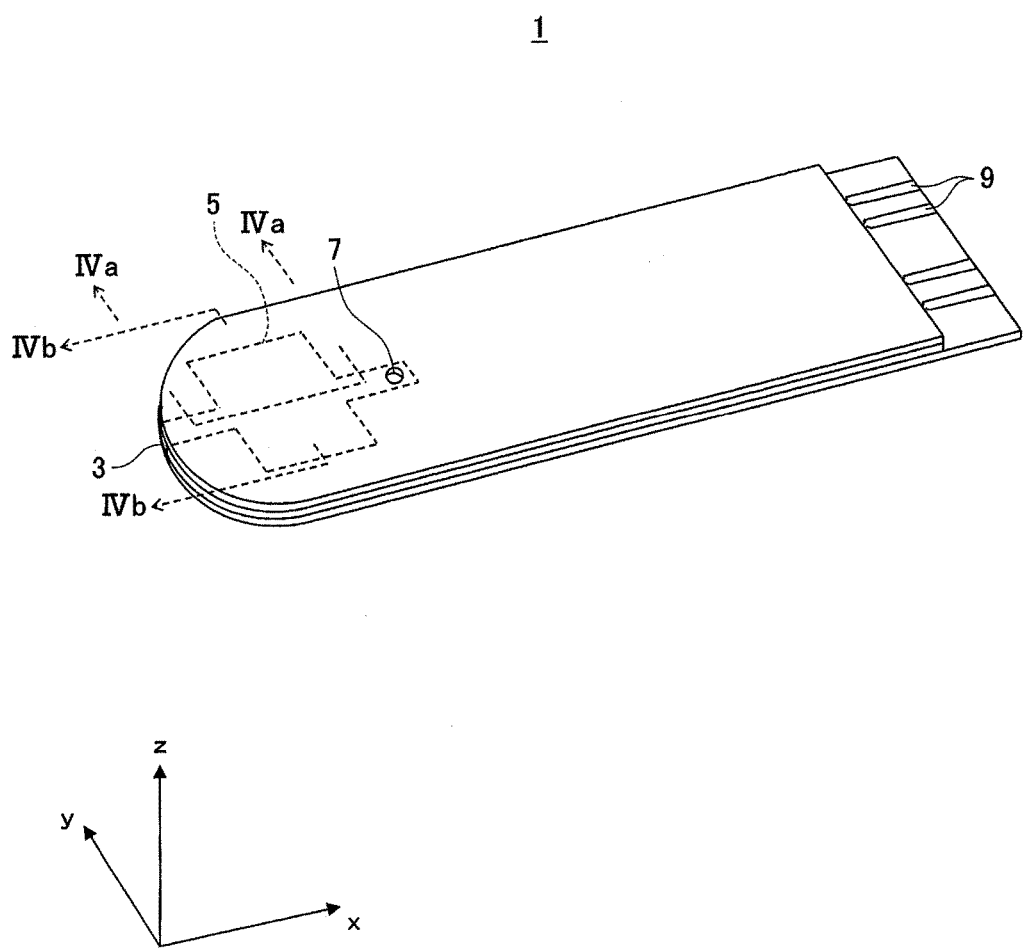
FIG. 1 is a perspective view showing a sensor according to a first embodiment of the present invention.

FIG. 1 is a perspective view showing a sensor 1 (analyte liquid sensor) according to a first embodiment.

The sensor 1 is for example formed in a roughly rectangular plate shape as a whole. The thickness thereof is for example 0.5 mm to 3 mm, the length in the x-direction is for example 1 cm to 5 cm, and the length in the y-direction is for example 1 cm to 3 cm.

In the sensor 1, an inflow port 3 for taking in the analyte liquid, a passage 5 in which the analyte liquid from the inflow port 3 flows, and an exhaust port 7 for exhausting gas of the passage 5 along with the inflow of the analyte liquid into the passage 5 are formed. Further, the sensor 1 is provided with a plurality of terminals 9 which are provided for input and output of electrical signals.

The inflow port 3 for example opens at one end of the rectangular shape of the sensor 1. The passage 5 for example extends in the longitudinal direction of the rectangular shape. The exhaust port 7 for example opens at the upper surface of the sensor 1. The plurality of terminals 9 are for example positioned on the other end of the rectangular shape.

The sensor 1 is for example attached to a not shown reader including an oscillation circuit etc. It is attached for example by inserting the end part of the sensor 1 on the terminal 9 side into a slot of the reader. The sensor 1 changes the electrical signal which is input to any one of the plurality of terminals 9 from the reader in accordance with the property or components of the analyte liquid taken in from the inflow port 3 and outputs the result to the reader from any one of the plurality of terminals 9. The sensor 1 is for example a disposable sensor.

Figure 2:
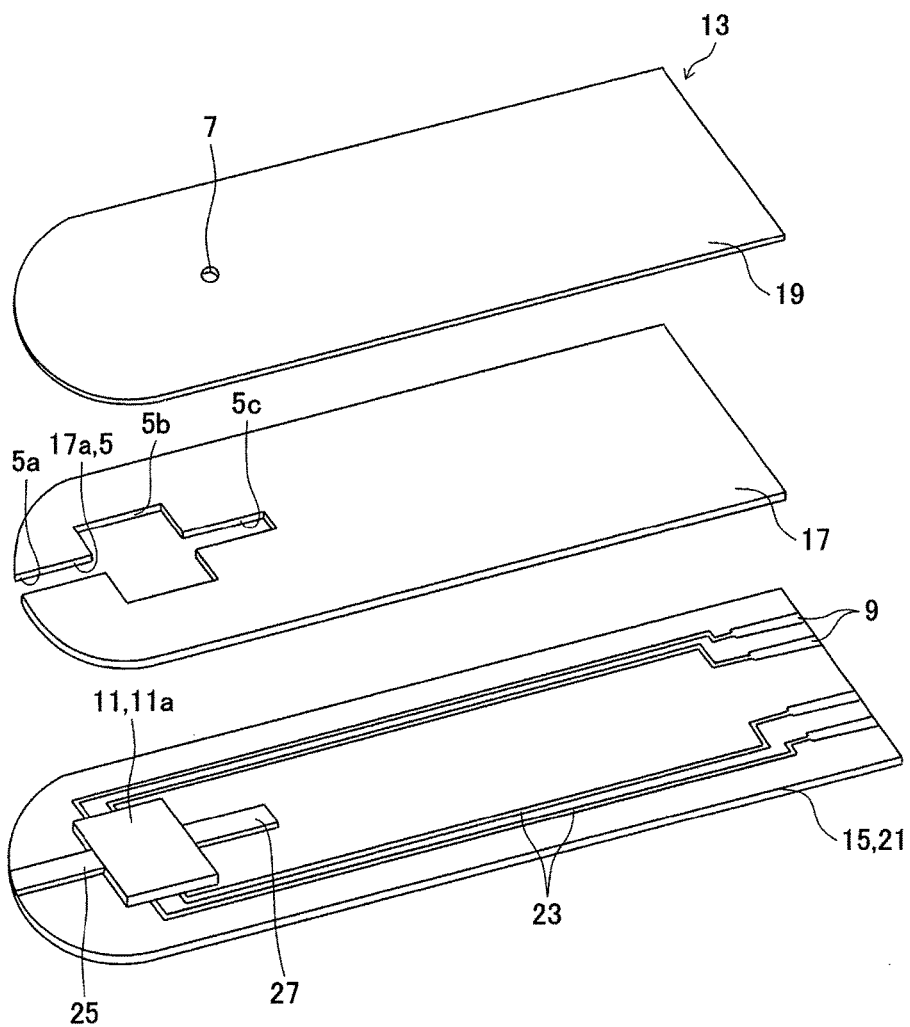
FIG. 2 is a disassembled perspective view of the sensor in FIG. 1.

FIG. 2 is a disassembled perspective view of the sensor 1.

The sensor 1 has a sensor element 11 and a package 13 which accommodates the sensor element 11. The sensor element 11 substantially performs the conversion of the electrical signal in accordance with the analyte liquid. The package 13 contributes to improvement etc. of the handling ability of the sensor element 11.

The sensor element 11 is for example formed in a roughly box state. Its upper surface becomes an element surface 11a to which the analyte liquid is supplied. The sensor element 11 converts the electrical signal in accordance with the property or components of the analyte liquid on the element surface 11a.

The package 13 for example has a lower layer member 15, intermediate layer member 17, and upper layer member 19 which have layer-shapes and are stacked in order from the lower side. In the intermediate layer member 17, a cut away portion 17a is formed. Due to this, between the lower layer member 15 and the upper layer member 19, a space for accommodating the sensor element 11 and the passage 5 are formed.

The lower layer member 15 is for example given the same configuration as that of a printed circuit board. An insulating base 21 thereof is for example configured by mainly using a resin or ceramic. The planar shape of the insulating base 21 is for example the same as the planar shape of the entire sensor 1. On the upper surface of the insulating base 21, the sensor element 11 is arranged. The sensor element 11 is for example fixed on the upper surface of the insulating base 21 by an adhesive. The lower layer member 15 has, on its upper surface, the already explained plurality of terminals 9 and a plurality of lines 23 for connecting the plurality of terminals 9 and the sensor element 11.

The intermediate layer member 17 is for example configured by an insulating material such as a resin or ceramic. The intermediate layer member 17 is for example adhered to the lower layer member 15 by an adhesive. The planar shape (schematic shape) of the intermediate layer member 17 is made a rectangle a little shorter than the lower layer member 15 so that the plurality of terminals 9 are exposed.

The upper layer member 19 is for example configured by a hydrophilic film. Accordingly, the upper layer member 19 for example becomes high in wettability with respect to the analyte liquid compared with the lower layer member 15 and intermediate layer member 17. Note that, the degree of wettability (or hydrophilic property) with respect to the analyte liquid, as generally known, can be measured by a contact angle with the analyte liquid. That is, the higher the wettability, the smaller the contact angle. The upper layer member 19 is for example adhered to the intermediate layer member 17 by an adhesive. The planar shape of the upper layer member 19 is, in the same way as the intermediate layer member 17, made a rectangle a little shorter than the lower layer member 15. Further, in the upper layer member 19, the already explained exhaust port 7 is formed.

As the hydrophilic film, use can be made of a commercially available resin film treated to make it hydrophilic (hydrophilic treatment). For example, use may be made of a resin film having a surface coated by a hydrophilic material. The resin which becomes the base material is for example polyester-based or polyethylene-based. The hydrophilic material is for example polyethylene glycol, phosphorylcholine, polyethylene oxide, or polyvinyl alcohol. Further, use may be made of a resin film made of a hydrophilic material (hydrophilic polymer) as well.

Note that, the sensor 1 for example does not have flexibility. For example, at least one of the lower layer member 15, intermediate layer member 17, and upper layer member 19 does not have flexibility.

The thickness of the intermediate layer member 17 is greater than the thickness of the sensor element 11. Accordingly, the cut away portion 17a forms a space 5b (see FIGS. 4A and 4B) on the sensor element 11 into which the analyte liquid flows. The passage 5 configured by the cut away portion 17a includes this space 5b, an inflow passage 5a for inflow of the analyte liquid to the space 5b, and an outflow passage 5c for outflow of the analyte liquid from the space 5b.

The upper surface of the insulating base 21 is provided with an inflow side lower surface member 25 configuring the lower surface of the inflow passage 5a and with an outflow side lower surface member 27 configuring the lower surface of the outflow passage 5c. These members are, for example, configured by hydrophilic films in the same way as the upper layer member 19. Accordingly, the lower surfaces of the inflow passage 5a and outflow passage 5c become smaller in contact angle with the analyte liquid compared with the lower layer member 15 and intermediate layer member 17.

Figure 4A:
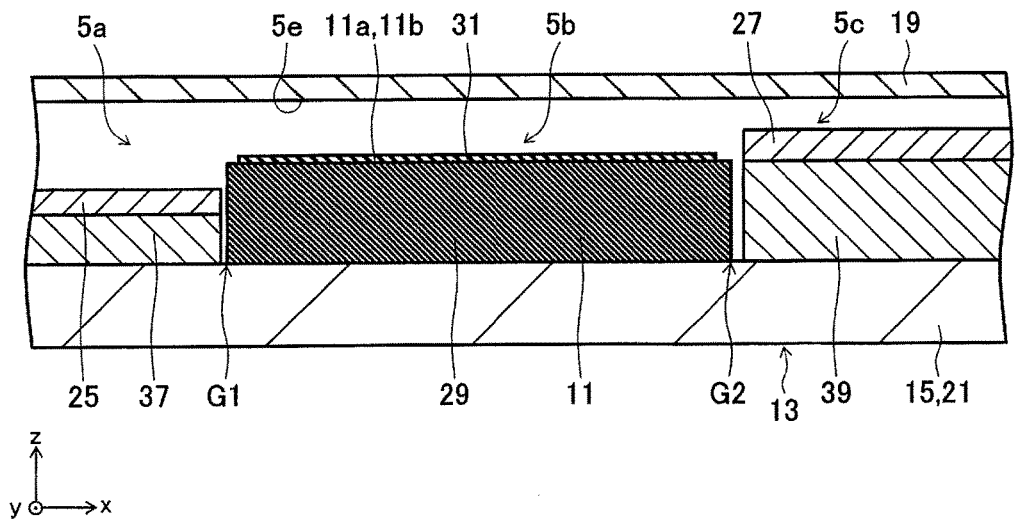
FIG. 4A is a cross-sectional view taken along an IVa-IVa line in FIG. 1.
Figure 4B:
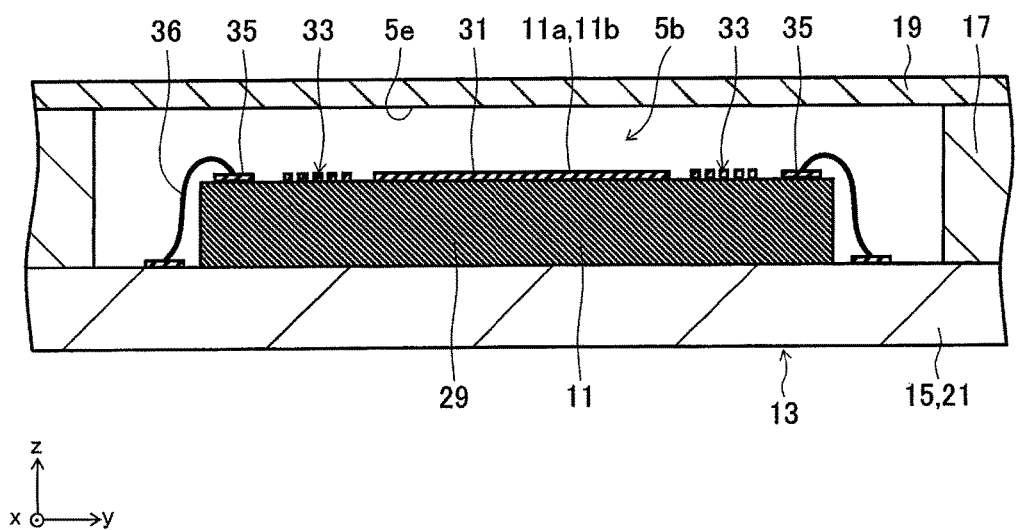
FIG. 4B is a cross-sectional view taken along an IVb-IVb line in FIG. 1.

The inflow side lower surface member 25 is for example fixed to the lower layer member 15 by an inflow side adhesive 37 (see FIGS. 4A and 4B). The outflow side lower surface member 27 is for example fixed to the lower layer member 15 by an outflow side adhesive 39 (see FIGS. 4A and 4B).

The inflow passage 5a for example linearly extends from the inflow port 3 to the space 5b with a constant width (y-direction). Further, the outflow passage 5c for example linearly extends with a constant width from the space 5b to the side opposite to the inflow port 3 (to the advancing direction of the analyte liquid). The width of the inflow passage 5a and the width of the outflow passage 5c are for example the same as each other and are smaller than the width of the space 5b.

The passage 5 is set relatively small in height in the z-direction. For example, the height of the passage 5 in the z-direction is 50 µm to 0.5 mm. From the viewpoint of reducing the amount of the analyte liquid (for example reducing the amount of collection of blood), the height of the passage 5 is preferably about 50 µm. Further, as explained above, the upper surface of the passage 5 (ceiling surface, lower surface of the upper layer member 19, etc.) is hydrophilic and consequently is small in contact angle with the analyte liquid.

Since the height of the passage 5 in the z-direction is small and the contact angle with the analyte liquid on the upper surface and lower surface of the passage 5 (inner surfaces of the passage 5) is small, when the analyte liquid contacts the inflow port 3, the analyte liquid flows in the inflow passage 5a toward the sensor element 11 due to the capillary phenomenon. That is, in the present embodiment, the work of using a micropipette or another tool to suck in the analyte liquid and inject the sucked in analyte liquid into the inflow port 3 is unnecessary.

Note that, the capillary phenomenon can be caused if the contact angle on the inner surface of the passage 5 is less than 90°. Accordingly, the wettability (hydrophilic property) of the inner surface of the passage 5 only has to have the highness at which the contact angle of the analyte liquid (it may be represented by water) becomes less than 90°. Further, from the viewpoint of reliably causing the capillary phenomenon, the wettability of the inner surface of the passage 5 preferably has the highness at which the contact angle becomes less than 60°. This same is true for the element surface 11a.

Figure 3:
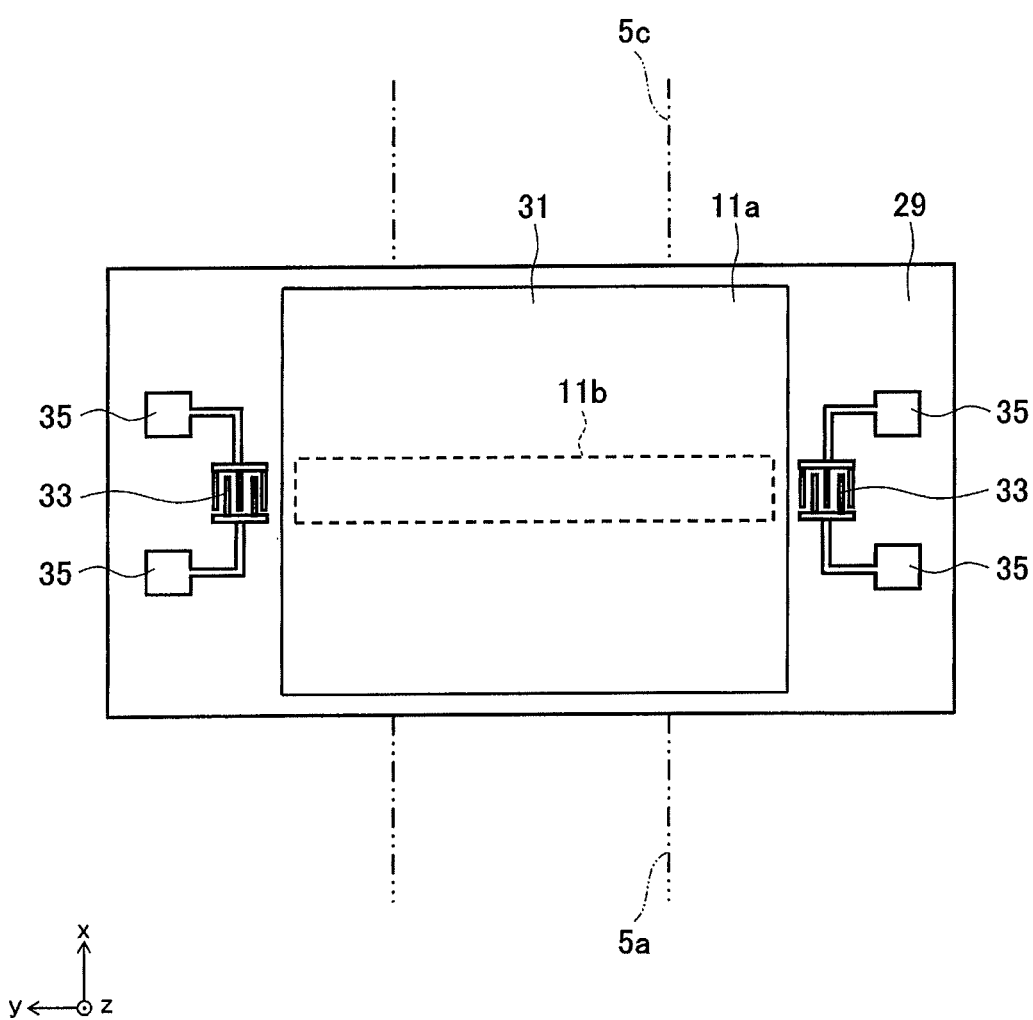
FIG. 3 is a plan view showing a sensor element of the sensor in FIG. 1.

FIG. 3 is a plan view showing the sensor element 11.

The sensor element 11 is for example configured by a SAW sensor element utilizing a SAW (Surface Acoustic Wave). The sensor element 11 for example has a piezoelectric substrate 29, and a metal film 31, a pair of IDT electrodes 33, and a plurality of pads 35 which are provided on the piezoelectric substrate 29.

The piezoelectric substrate 29 is for example made of a substrate of a single crystal having a piezoelectric property such as a lithium tantalate ($LiTaO_3$) single crystal, lithium niobate ($LiNbO_3$) single crystal or quartz crystal. The planar shape and various dimensions of the piezoelectric substrate 29 may be suitably set. As an example, the thickness of the piezoelectric substrate 29 is 0.3 mm to 1.0 mm.

The metal film 31 is for example given a roughly rectangular planar shape, positioned at the center in the y-direction and provided over roughly the entire x-direction on the upper surface of the piezoelectric substrate 29. The metal film 31 for example has a two layer structure of chromium and gold which is formed on the chromium. On the surface of the metal film 31, for example, an aptamer made of nucleic acid or peptide is arranged (fixed).

The pair of IDT electrodes 33 are for generating the SAW which is propagated on the upper surface of the piezoelectric substrate 29 and for receiving this SAW. The pair of IDT electrodes 33 are arranged while sandwiching the metal film 31 therebetween. That is, the metal film 31 is positioned in the propagation path of the SAW. The direction of arrangement of the metal film 31 and pair of IDT electrodes 33 is for example a direction crossing the passage 5 (more specifically crossing at a right angle).

Each IDT electrode 33 has a pair of comb-shaped electrodes. Each comb-shaped electrode has a bus bar and a plurality of electrode fingers extending from the bus bar. The pair of comb-shaped electrodes are arranged so that their plurality of electrode fingers mesh with each other. The pair of IDT electrodes 33 configures a transversal type IDT electrode.

The frequency characteristic can be designed by using the number of electrode fingers of the IDT electrode 33, distance between the electrode fingers adjacent to each other, crossing width of the electrode fingers, and so on as parameters. As the SAW excited by the IDT electrodes, there are a Rayleigh wave, Love wave, Leakey wave, and so on. Any of them may be utilized.

An elastic member for suppressing reflection of the SAW may be provided at an outside region other than the pair of IDT electrodes 33 in the propagation direction of the SAW. The frequency of the SAW can be set within a range of for example from several megahertz (MHz) to several gigahertz (GHz). In particular, a range of from several hundred MHz to 2 GHz is practical. If so, reduction of size of the piezoelectric substrate 29 and consequently reduction of size of the sensor element 11 can be realized.

The plurality of pads 35 are connected to the IDT electrodes 33. Further, the plurality of pads 35 are for example connected through bonding wires 36 (see FIG. 4B) to the lines 23 of the lower layer member 15. A signal input from the terminal 9 is input through a pad 35 to an IDT electrode 33, while a signal output from an IDT electrode 33 is output through a pad 35 to a terminal 9.

The IDT electrodes 33, pads 35, and lines connecting them are for example made of gold, aluminum, an alloy of aluminum and copper, or the like. These conductors may be given a multi-layer structure as well. In the case of a multi-layer structure, for example, the first layer may be made of titanium or chromium, the second layer may be made of aluminum, aluminum alloy, or gold, and, further, the uppermost layer may have titanium or chromium laminated on it. Note that, thicknesses of these conductors are for example less than 1 µm, so the influence exerted upon the height of the passage 5 (for example 50 µm or more) is small.

When the analyte liquid contacts the metal film 31 on which an aptamer is arranged, a specific target substance in the analyte liquid is bonded with the aptamer corresponding to that target substance, so the weight of the metal film 31 changes. As a result, the phase characteristic etc. of SAW propagated between the pair of IDT electrodes 33 change. Accordingly, the property or components of the analyte liquid can be checked based on that change of phase characteristic etc.

Note that, the metal film 31, mainly the region between the pair of IDT electrodes 33 in it, configures the detection part 11b. The already explained element surface 11a is the surface including the detection part 11b and is configured by the piezoelectric substrate 29, IDT electrodes 33, metal film 31, pads 35, and upper surfaces of lines etc.

FIG. 4A is a cross-sectional view taken along an IVa-IVa line in FIG. 1, while FIG. 4B is a cross-sectional view taken along an IVb-IVb line in FIG. 1.

As explained above, inside the package 13, an inflow passage 5a for inflow of the analyte liquid to the space 5b on the detection part 11b and an outflow passage 5c for outflow of the analyte liquid from the space 5b are formed.

All of the upper surfaces of the inflow passage 5a, space 5b, and outflow passage 5c are configured by the upper layer member 19 made of a hydrophilic film. Accordingly, their upper surfaces are continuous with respect to each other and form a continuous surface 5e. Note that, the "continuous" referred to here means that no gap or step exists in the side view of the passage. In the side view of the passage, the continuous surface 5e extends in straight line state or curved state approximating a straight line.

The lower surface of the inflow passage 5a is configured by the inflow side lower surface member 25, while the lower surface of the space 5b is configured by the element surface 11a. Accordingly, a gap G1 is formed between the two. In the same way, the lower surface of the space 5b is configured by the element surface 11a, and the lower surface of the outflow passage 5c is configured by the outflow side lower surface member 27, so a gap G2 is formed between the two. These gaps G1 and G2 become an obstacle for the analyte liquid which flows by the capillary phenomenon.

Therefore, the element surface 11a is made higher than the lower surface of the inflow passage 5a. In the same way, the lower surface of the outflow passage 5c is made higher than the element surface 11a. Such adjustment of the height is for example carried out by adjusting the thicknesses of the inflow side adhesive 37 and outflow side adhesive 39. In place of or addition to the adjustment of thicknesses of the adhesives, the height adjustment may be carried out according to the adjustment of thicknesses of the inflow side lower surface member 25 and outflow side lower surface member 27 as well.

More specifically, the upper surface of the piezoelectric substrate 29 is made higher than the lower surface of the inflow passage 5a. Consequently, the detection part 11b (and element surface 11a including the detection part 11b) positioned on the piezoelectric substrate 29 becomes higher than the lower surface of the inflow passage 5a.

Figure 5A:
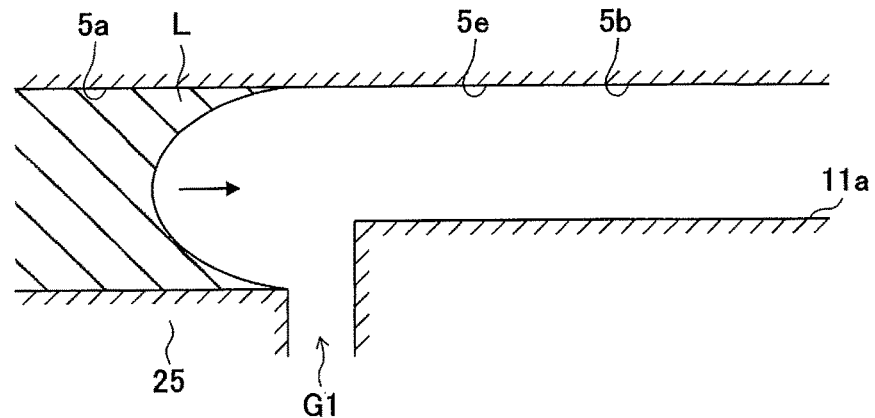
FIGS. 5A to 5C are schematic cross-sectional views for explaining the mode of operation of the sensor in FIG. 1.
Figure 5B:
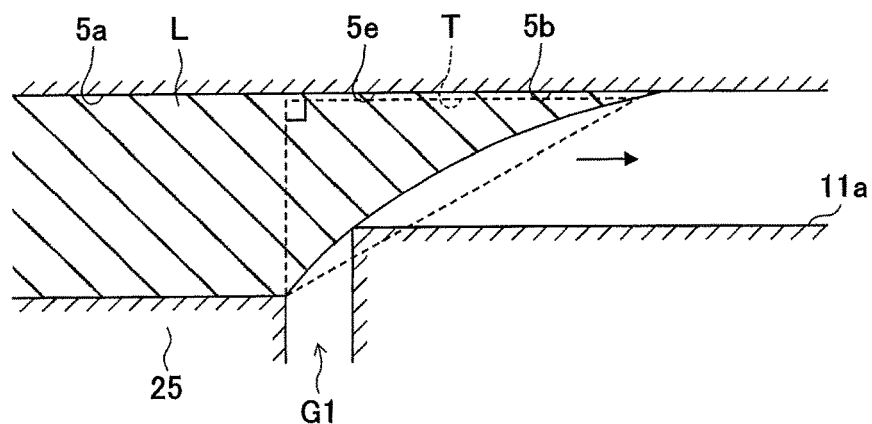
Figure 5C:
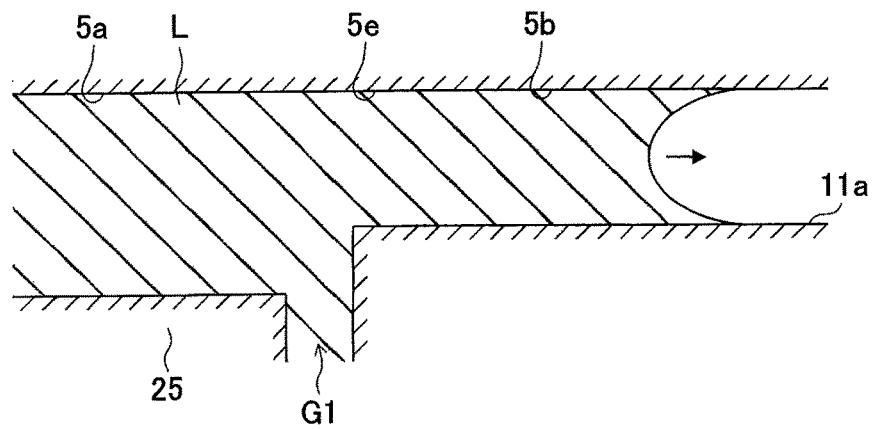

FIG. 5A to FIG. 5C are views for explaining the mode of operation of the sensor 1 and are schematic cross-sectional views near the gap G1.

As shown in FIG. 5A, an analyte liquid L taken from the inflow port 3 tries to wet the upper surface and lower surface of the inflow passage 5a and consequently flows in the inflow passage 5a toward the space 5b by the capillary phenomenon. Then, the analyte liquid L reaches the gap G1.

As shown in FIG. 5B, even when the analyte liquid L reaches the gap G1, on the upper surface side, the analyte liquid L advances so as to further wet the continuous surface 5e. On the other hand, on the lower surface side, due to interruption of the lower surface to be wetted, the advance of the analyte liquid L is stopped. Note that, the side surface of the inflow side lower surface member 25 is the transverse section of the hydrophilic film, so the wettability is generally low.

However, the element surface 11a becomes higher than the lower surface of the inflow passage 5a. Therefore, if the analyte liquid L on the upper surface side advances, the analyte liquid L contacts a portion of the element surface 11a (edge part on the gap G1 side in the present embodiment). Then, the analyte liquid L restarts the advance so as to wet the element surface 11a.

As a result, as shown in FIG. 5C, the analyte liquid flows in the space 5b by the capillary phenomenon.

The action of the analyte liquid passing over the gap G1 is facilitated since the higher the element surface 11a relative to the lower surface of the inflow passage 5a, the easier it becomes for the element surface 11a to touch the analyte liquid. Further, the action of the analyte liquid passing over the gap G1 is facilitated since the smaller the contact angle with the analyte liquid on the continuous surface 5e, the more the analyte liquid advances on the continuous surface 5e so as to try to wet the continuous surface 5e.

Here, as shown in FIG. 5B by the right-angled triangle T by a broken line, the surface of the analyte liquid L touching the element surface 11a can be approximated by the hypotenuse of the right-angled triangle T. By assuming this right-angled triangle T, the height etc. of the element surface 11a can be suitably set.

For example, in a case where assuming a predetermined contact angle to set the height of the element surface 11a, as the right-angled triangle T, a right-angled triangle (first right-angled triangle) having a perpendicular line of the continuous surface 5e drawn from the edge part of the lower surface of the inflow passage 5a on the gap G1 side to the continuous surface 5e as one adjacent side, having a line along the continuous surface 5e as the other adjacent side, and having the contact angle of the continuous surface 5e made the angle formed by the other adjacent side and the hypotenuse is assumed. The hypotenuse of this first right-angled triangle approximates the surface of the analyte liquid L which is in contact with the continuous surface 5e at a predetermined contact angle and which should touch the element surface 11a, therefore the height of the element surface 11a may be set so that a portion thereof abuts against the hypotenuse.

Specifically, for example, if the element surface 11a is higher than the lower surface of the inflow passage 5a by a difference which is larger than the product of the length of the gap G1 in the passage direction and the tangent of the contact angle, the edge part of the element surface 11a on the gap G1 side abuts against the hypotenuse of the first right-angled triangle.

Further, for example, in a case where assuming the height of the element surface 11a to set a contact angle of the analyte liquid (to select the material of the continuous surface 5e), as the right-angled triangle T, a right-angled triangle (second right-angled triangle) having a perpendicular line of the continuous surface 5e drawn from the edge part of the lower surface of the inflow passage 5a on the gap G1 side to the continuous surface 5e as one adjacent side, having a line along the continuous surface 5e as the other adjacent side, and having a line drawn from the edge part of the lower surface of the inflow passage 5a on the gap G1 side and abutting against a portion of the element surface 11a (edge part on the gap G1 side in the present embodiment) as the hypotenuse is assumed. The angle formed by the other adjacent side (continuous surface 5e) and by the hypotenuse in this second right-angled triangle approximates the maximum contact angle that the analyte liquid L can touch the element surface 11a, therefore the contact angle may become smaller than the angle formed by the other adjacent side described before (continuous surface 5e) and by the hypotenuse.

More directly, the contact angle may be smaller than the angle formed by the line (hypotenuse) which extends from the edge part of the lower surface of the inflow passage 5a on the gap G1 side so as to contact a portion of the element surface 11a and by the continuous surface 5e.

There are hydrophilic films etc. which is able to control the contact angle with water or the like to less than 10°. Note that, it is difficult to measure the contact angle within a range less than 10°, therefore specifying that the contact angle be less than 10° is substantially the same as specifying that the wettability be high to the maximum extent. The continuous surface 5e (and lower surfaces of various passages) preferably has a contact angle with the analyte liquid of less than 10°.

Incidentally, when assuming that the contact angle is 10°, for the edge part of the element surface 11a on the gap G1 side to abut against the hypotenuse of the first right-angled triangle, the element surface 11a only has to be higher than the inflow passage 5a by a difference obtained by multiplying the length of the gap G1 in the passage direction by tan 10°. tan 10° is about 0.18. Accordingly, when the contact angle is 10°, if the element surface 11a is higher than the inflow passage 5a by a difference not less than 20% of the length of the gap G1 in the passage direction, the action of the flow due to the capillary phenomenon passing over the gap G1 can be expected.

Note that, the flow between the inflow passage 5a and the space 5b was explained, but the flow between the space 5b and the outflow passage 5c is the same as well.

As described above, in the present embodiment, at least a portion (in the present embodiment, all) of the lower surface (element surface 11a) on the downstream side from the gap G1 becomes higher than the lower surface on the upstream side from the gap G1 (lower surface of the inflow passage 5a). Accordingly, the analyte liquid which has advanced on the upper surface side so as to wet the continuous surface 5e can be made to pass over the gap G1 and touch a portion (edge part) of the element surface 11a, and the flow due to the capillary phenomenon can be made to continue to the element surface 11a side.

Second Embodiment

Figure 6A:
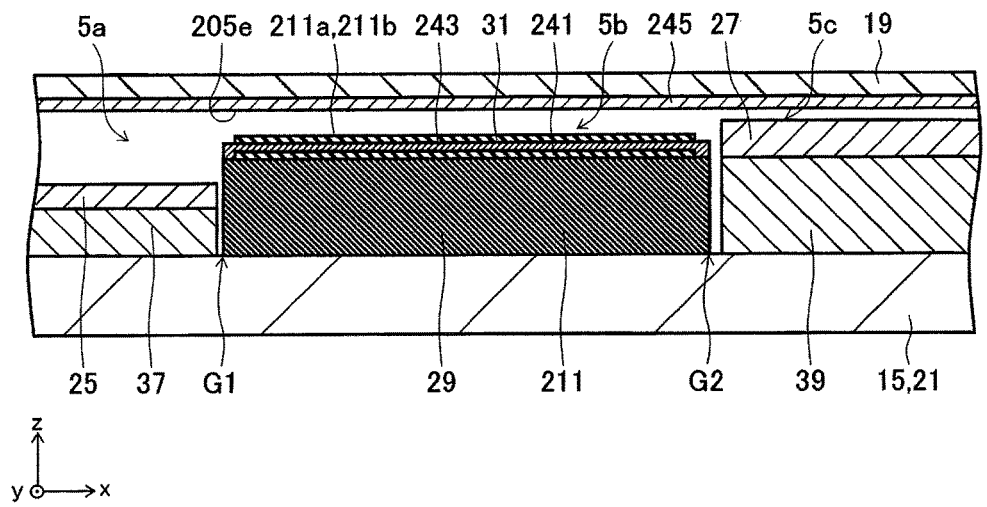
FIG. 6A and FIG. 6B are cross-sectional views showing a sensor according to a second embodiment of the present invention.
Figure 6B:
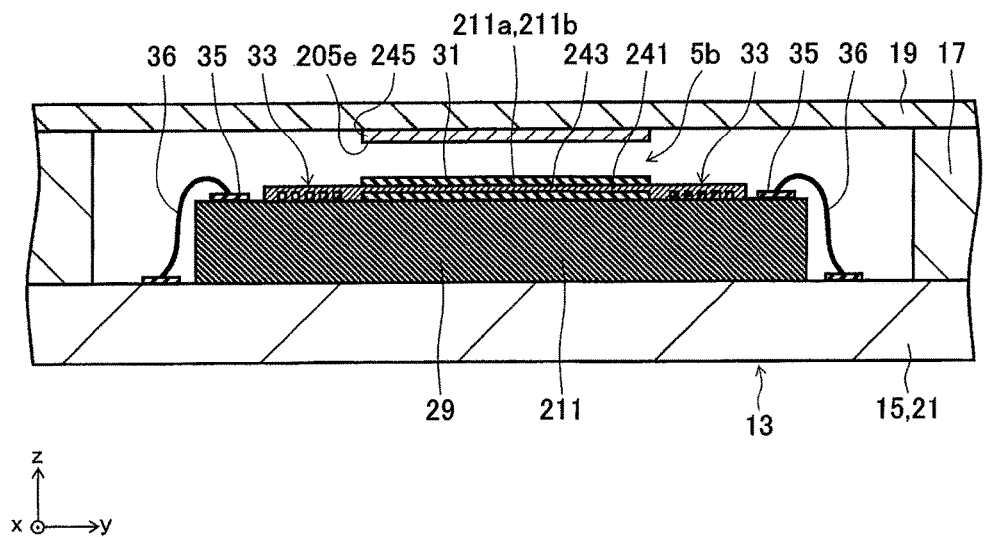

FIG. 6A and FIG. 6B are cross-sectional views corresponding to FIG. 4A and FIG. 4B and show a sensor 201 according to a second embodiment of the present invention.

The sensor 201 differs from the first embodiment in the point that a sensor element 211 has a short-circuiting electrode 241 and protective film 243 and a point that a convex portion 245 is provided on a continuous surface 205e in a front view of the passage. Specifically, this is as follows.

The short-circuiting electrode 241 is provided on the upper surface of the piezoelectric substrate 29, between a pair of IDT electrodes 33. The protective film 243 covers the upper surface of the piezoelectric substrate 29 from the top of the pair of IDT electrodes 33 and short-circuiting electrode 241. The metal film 31 is provided on the protective film 243.

The short-circuiting electrode 241 is for electrically short-circuiting the portion which becomes the propagation path of the SAW at the upper surface of the piezoelectric substrate 29. By providing this short-circuiting electrode 241, depending on the type of the SAW, the loss of the SAW can be made smaller. Note that, it is considered that the effect of suppression of loss by the short-circuiting electrode 241 is particularly high when using a Leakey wave as the SAW. The short-circuiting electrode 241 is for example formed over a range equal to the range of the detection part 11b which is shown by the dotted line in FIG. 3. The short-circuiting electrode 241 may be rendered an electrically floating state or may be given a ground potential.

The protective film 243 for example covers substantially the entire piezoelectric substrate 29 except the region for arrangement of the pads 35 and contributes to prevention of oxidation of the conductors such as the pair of IDT electrodes 33 and short-circuiting electrode 241. The protective film 243 is for example made of an inorganic insulating material. The inorganic insulating material is for example a silicon oxide (for example $SiO_2$), aluminum oxide, zinc oxide, titanium oxide, silicon nitride, or silicon. Note that, the thickness of the protective film 243 (height from the upper surface of the piezoelectric substrate 29) is for example greater than the thickness of the IDT electrode 33 or another conductor. Further, the thickness of the protective film 243 is for example 200 nm to 10 μm.

The convex portion 245 is configured by for example adhering a hydrophilic film to the lower surface of the upper layer member 19. The contact angle with the analyte liquid on the lower surface of the convex portion 245 is preferably not more than the contact angle with the analyte liquid on the lower surface of the upper layer member 19. The convex portion 245 for example extends over the inflow passage 5a, space 5b, and outflow passage 5c with a width equal to the metal film 31.

In the second embodiment as well, in the same way as the first embodiment, the element surface 211a (including a detection part 211b) is made higher than the lower surface of the inflow passage 5a, therefore the analyte liquid can be made to flow so as to pass over the gap G1 in the same way as the first embodiment.

The protective film 243 contributes to making the element surface 211a higher than the lower surface of the inflow passage 5a depending on its thickness. The thickness of the protective film 243 can be relatively easily adjusted in the thin film formation by CVD etc., therefore the adjustment of the height of the element surface 211a is facilitated.

On the convex portion 245, the distance from the element surface 211a becomes short, therefore the capillary phenomenon becomes more likely to occur. Accordingly, for example, by making the analyte liquid flow on the detection part 211b more than the lateral side of the space 5b, formation of air bubbles on the detection part 211b can be suppressed. The effect is conspicuous at the time when the contact angle with the analyte liquid on the lower surface of the convex portion 245 is smaller than the contact angle with the analyte liquid on the surface adjacent to the lateral side thereof.

(Modifications)

Figure 7A:
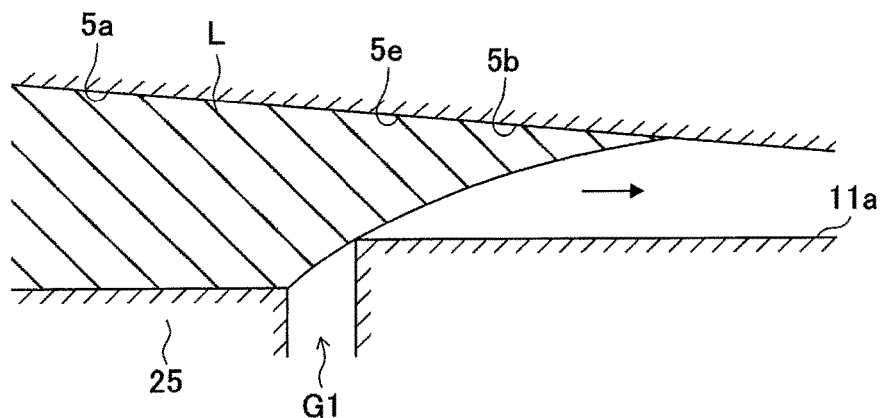
FIG. 7A to FIG. 7C are schematic views for explaining modifications.
Figure 7B:
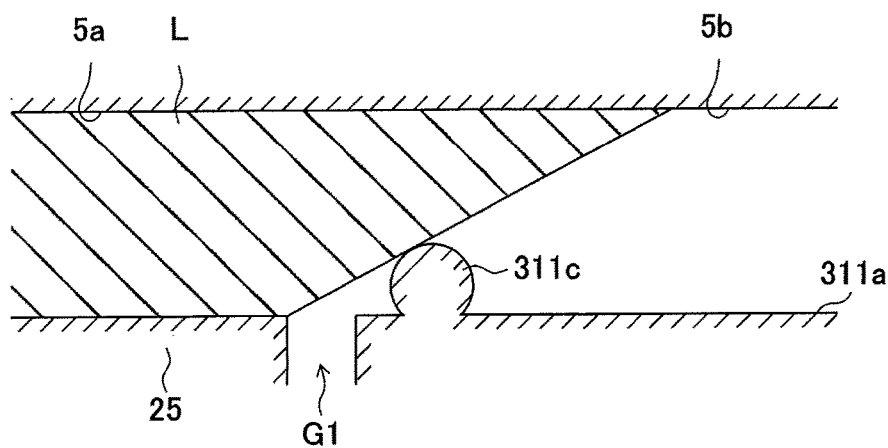
Figure 7C:
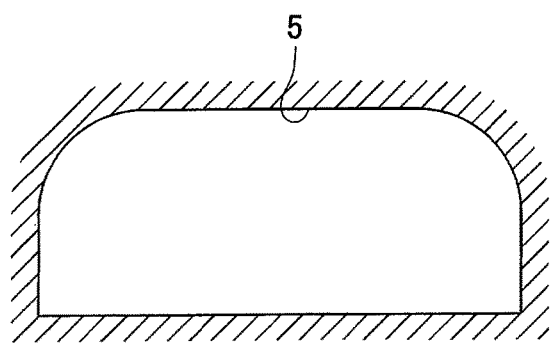

FIG. 7A to FIG. 7C are schematic cross-sectional views showing modifications of the passage shape etc.

FIG. 7A is a cross-sectional view of the passage seen from the side in the same way as FIGS. 5A to 5C. In this modification, the continuous surface 5e is inclined. Specifically, it is inclined so that the height of the space 5b becomes lower than the height of the inflow passage 5a. Such an inclination is realized by suitably adjusting the thickness of the intermediate layer member 17 or making the upper layer member 19 warp in the space 5b having an area broader than the inflow passage 5a. Where the continuous surface 5e is inclined in this way, for example, it is expected that the analyte liquid L will be able to pass over the gap G1 more easily.

FIG. 7B shows a cross-sectional view of the passage seen from the side in the same way as FIGS. 5A to 5C. In this modification, the element surface 311a as a whole does not become higher than the lower surface of the inflow passage 5a. By formation of the convex portion 311c on the element surface 311a, only a portion of the element surface 311a becomes higher than the lower surface of the inflow passage 5a. The convex portion 311c is for example formed by arranging a metal or resin on the piezoelectric substrate 29. In such an aspect as well, when the analyte liquid touches the convex portion 311c, the analyte liquid tries to wet the convex portion 311c, so the flow of the analyte liquid on the lower surface side is restarted.

FIG. 7C shows a cross-sectional view of the passage seen from the front. Note that, this cross-sectional view may show the cross-section at any position among the inflow passage 5a, space 5b, and outflow passage 5c. In this modification, in the passage 5, corner portions on the lateral sides of the upper surface are chamfered to form curved surfaces. Such chamfering is for example realized by forming an inclined surface on the side surface configuring a cut away portion 17a when forming the cut away portion 17a in the intermediate layer member 17. In this modification, the height of the passage becomes low in the chamfered portions, and the analyte liquid can pass over the gap at these positions more easily. On the other hand, in this modification, compared with the case where the entire upper surface is made low, the passage area is easily secured.

The present invention is not limited to the above embodiments and may be executed in various ways.

The sensor is not limited to one utilizing a SAW. For example, it may be one utilizing surface plasmon resonance or one utilizing vibration of a quartz crystal unit. Further, the sensor is not limited to a biosensor. From another viewpoint, the detection part is not limited to one on which an aptamer is arranged. For example, the detection part may be configured by an electrode for measuring pH based on a change of potential as well.

Further, when the sensor is one utilizing a SAW, several pairs of IDT electrodes may be arranged in the flow direction. In this case, the type of the aptamer which is arranged between each pair of IDT electrodes can be changed to perform several types of measurement or measurement can be carried out by comparing a pair of IDT electrodes between which an aptamer is arranged with a pair of IDT electrodes between which an aptamer is not arranged.

Further, the sensor may be used for any application. In other words, any type of specimen (analyte liquid) may be used. For example, the type of specimen may be a bodily fluid (for example blood), may be a beverage, may be a liquid medicine, or may be water not pure water (for example seawater, lake water, or ground water). Further, for example, the type of specimen may be one containing water or one containing oil. Further, for example, the type of specimen may be a solution or sol.

Note that, in one type of specimen, the individual specimens will have indefiniteness with respect to components etc. For example, when the type of specimen is blood, the quantities of the components contained in that blood will differ according to the person (according to each specimen). It is for this reason that blood is measured by the sensor. Accordingly, strictly speaking, the contact angle with the specimen on the inner surface of the passage differs for each specimen.

In general, however, that difference is very small. Alternatively, a sensor utilizing the capillary phenomenon is configured so that the difference will not become the problem. Accordingly, for example, the contact angle with the specimen on the inner surface of the passage of the sensor may be judged according to the contact angle with each specimen or may be judged according to the contact angle with a specimen having a standard composition. Note that, in a case where there is an abnormal specimen, the latter is preferred. Further, when the type of specimen is a solution and the solvent is water, it is considered that usually the contact angle with the specimen may be judged according to the contact angle with water.

The passage in which the analyte liquid flows may be suitably configured other than as illustrated in the embodiments. For example, in the embodiments, the inflow port 3 opened at the end face of the package 13, but it may open at the upper surface of the package 13 as well. Further, for example, in the embodiments, the exhaust port 7 opened at the upper surface of the package 13, but it may open at the end face of the package 13 as well. Further, for example, in the embodiments, the widths of the inflow passage 5a and outflow passage 5c were made narrower than the width of the space 5b, but may be equal to the width of the space 5b as well.

Further, for example, the passage does not have to include both of the inflow passage and outflow passage. Here, it is apparent that the outflow passage is not indispensable. For example, an exhaust port may be formed adjacent to the space on the element surface as well.

Further, when both of the inflow passage and outflow passage are provided, the configuration where the lower surface on the downstream side from the gap (concave portion) becomes higher than the lower surface on the upstream side from the gap does not have to be applied to both of the inflow passage and the outflow passage and may be applied to only one of them.

The passage may be formed by suitable members. For example, the intermediate layer member may be configured by two layers, the first layer which is arranged on the lower layer member may have a shape formed with a hole for arranging the sensor element, the second layer to be arranged on that may have a shape formed with a hole for arranging the sensor element and a cut away portion corresponding to the inflow passage, and the inflow side lower surface member 25 in the embodiments may be omitted.

The method of making the wettability of the inner surface of the passage higher is not limited to the method of arranging a hydrophilic film. For example, the base material may be treated to make it hydrophilic as well. As the hydrophilic treatment, for example, there can be mentioned a method of arranging (fixing) a coating agent. More specifically, for example, the base material may be treated by ashing by oxygen plasma, a silane coupling agent may be coated, and polyethylene glycol may be coated as the coating agent. Further, for example, the base material may be treated on its surface by using a processing agent having phosphorylcholine. The phosphorylcholine may be fixed as the coating agent.

In the second embodiment, the explanation was given focusing on that point that a convex portion is formed on the upper surface of the passage. From the second embodiment, it is possible to extract the feature of partially making the contact angle with the analyte liquid on the upper surface of the passage change in the width direction of the passage. When applying this feature, the region in which the contact angle with the analyte liquid is small does not always have to be the surface of the convex portion. In other words, instead of sticking the hydrophilic film on the lower surface of the upper layer member, a hydrophilic treatment (or hydrophobic treatment) may be applied to the lower surface of the upper layer member to form a region in which the contact angle with the analyte liquid is small at a suitable position (for example position facing the detection part).

When forming a flow which passes over the first gap (gap G1 in the embodiments), it is also effective if the upper surface of the piezoelectric substrate is higher than the lower surface of the inflow passage, and it is also effective if the upper surface of the element surface is higher than the lower surface of the inflow passage. Note that, the surface in the case where a predetermined configuration is added to the upper surface of the piezoelectric substrate is the element surface. As the additional configuration, the detection part, IDT, protective layer (SiO₂), etc. are included. The upper surface of the piezoelectric substrate as a whole need not be higher than the lower surface of the inflow passage. Only a portion may be higher than the latter.

The gap (concave portion) of the lower surface of the passage is not limited to a gap between the sensor element and the package. In other words, the configuration where the feature is applied of making the lower surface on the downstream side from the gap higher than the lower surface on the upstream side from the gap is not limited to a combination of the lower surface of the inflow passage and the element surface or a combination of the element surface and the outflow passage. The feature described before may be applied to the lower surfaces before and behind any gap which is formed due to configuring the package from a plurality of members. Even in such a case, the effect of the analyte liquid passing over the gap is exhibited.

REFERENCE SIGNS LIST

1 . . . sensor, 5a . . . inflow passage, 5b . . . space, 5e . . . continuous surface, 11 . . . sensor element, 11a . . . element surface, 11b . . . detection part, 13 . . . package, and G1 . . . gap (concave portion).

The invention claimed is:

1. A sensor, comprising:
   a sensor element comprising an element surface having a first end and a second end, the sensor element being configured to output a signal in accordance with a detected object contained in a specimen positioned at a detection part in the element surface; and
   a package configured to accommodate the sensor element in an internal portion thereof and comprising a passage including an inflow passage, an outflow passage and a space located between the inflow and outflow passages, wherein the element surface is located within the space, and wherein
   a lower surface of the passage comprises the element surface and a lower surface of the inflow passage and a lower surface of the outflow passage,
   a first gap is positioned between the lower surface of the inflow passage and the first end of the element surface, wherein the first gap runs substantially perpendicular to the lower surface of the inflow passage,
   the lower surface of the inflow passage does not include a lower surface of the first gap,
   the element surface is positioned such that it is higher than the lower surface of the inflow passage and the lower surface of the outflow passage is positioned higher than the element surface.

2. The sensor according to claim 1, wherein
   the sensor element comprises a piezoelectric substrate, the piezoelectric substrate comprising, on an upper surface thereof, the detection part of the element surface and a pair of IDT electrodes positioned on two sides of the detection part, and
   at least a portion of the upper surface of the piezoelectric substrate is positioned above the lower surface of the inflow passage.

3. The sensor according to claim 1, wherein the detection part has an aptamer.

4. The sensor according to claim 1, wherein, in a side view of the inflow passage, a contact angle with the specimen on an upper surface of the passage is smaller than an angle which is formed by a straight line and the upper surface of the passage, the straight line extending from an edge part on a side of the first gap in the lower surface of the inflow passage so as to contact the portion of the element surface.

5. The sensor according to claim 4, wherein the contact angle with the specimen on the upper surface of the passage is less than 10°.

6. The sensor according to claim 1, wherein
   the lower surface of the passage further comprises the lower surface of an outflow passage extending from the space to a direction different from the inflow passage,
   a second gap is positioned between the element surface and the lower surface of the outflow passage.

7. The sensor according to claim 1, wherein
   the package comprises
      a lower layer member, and
      an inflow side lower surface member which is bonded onto the lower layer member by an adhesive and configures the lower surface of the inflow passage, and
   the element surface is positioned above the lower surface of the inflow passage by a difference which is larger than a product of the length in the passage direction of the first gap and a tangent of a contact angle with the specimen on an upper surface of the passage.

8. A sensor, comprising:
   a sensor element comprising an element surface having a first end and a second end, the sensor element being configured to output a signal in accordance with a detected object contained in a specimen positioned at a detection part in the element surface; and
   a package configured to accommodate the sensor element in an internal portion thereof and comprising a passage including an inflow passage, an outflow passage and a space located between the inflow and outflow passages, wherein the element surface is located within the space, and wherein
   a lower surface of the passage comprises the element surface and a lower surface of the outflow passage extending from the space to an advancing direction of the specimen,
   a gap is positioned between the second end of the element surface and the lower surface of the outflow passage, wherein the gap runs substantially perpendicular to the lower surface of the outflow passage,
   the lower surface of the inflow passage does not include a lower surface of the gap,
   the element surface is positioned above the lower surface of the inflow passage, and
   the lower surface of the outflow passage is positioned above the element surface.

* * * * *